(12) United States Patent
Duma et al.

(10) Patent No.: US 9,797,821 B2
(45) Date of Patent: Oct. 24, 2017

(54) METHODOLOGY FOR ASSESSING THE BIOMECHANICAL PERFORMANCE OF HELMETS

(71) Applicants: Stefan M. Duma, Blacksburg, VA (US); Steven Rowson, Blacksburg, VA (US); Craig McNally, Dublin, VA (US)

(72) Inventors: Stefan M. Duma, Blacksburg, VA (US); Steven Rowson, Blacksburg, VA (US); Craig McNally, Dublin, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 14/806,595

(22) Filed: Jul. 22, 2015

(65) Prior Publication Data

US 2016/0021964 A1 Jan. 28, 2016

Related U.S. Application Data

(60) Provisional application No. 62/027,492, filed on Jul. 22, 2014.

(51) Int. Cl.
*G01M 7/08* (2006.01)
*G01N 3/30* (2006.01)
*A42B 3/04* (2006.01)

(52) U.S. Cl.
CPC ............... *G01N 3/30* (2013.01); *G01M 7/08* (2013.01); *A42B 3/046* (2013.01)

(58) Field of Classification Search
None
See application file for complete search history.

(56) References Cited

U.S. PATENT DOCUMENTS

| | | | | |
|---|---|---|---|---|
| 3,331,236 | A * | 7/1967 | Payne | G01N 3/30 73/12.04 |
| 2004/0074283 | A1* | 4/2004 | Withnall | G01N 3/32 73/12.12 |
| 2015/0040685 | A1* | 2/2015 | Nicholson | A61B 5/4064 73/862.51 |
| 2015/0046116 | A1* | 2/2015 | Eatwell | G01L 5/0052 702/150 |

\* cited by examiner

*Primary Examiner* — Robert R Raevis
(74) *Attorney, Agent, or Firm* — Vogt IP

(57) ABSTRACT

The present invention provides a method for testing a helmet that uses a risk function that incorporates both linear and rotational acceleration to predict the helmet's ability to prevent a concussion. In certain embodiments, the testing matrix includes 3 impact energy levels and 4 impact locations, for a total of 12 testing conditions per helmet.

20 Claims, 12 Drawing Sheets

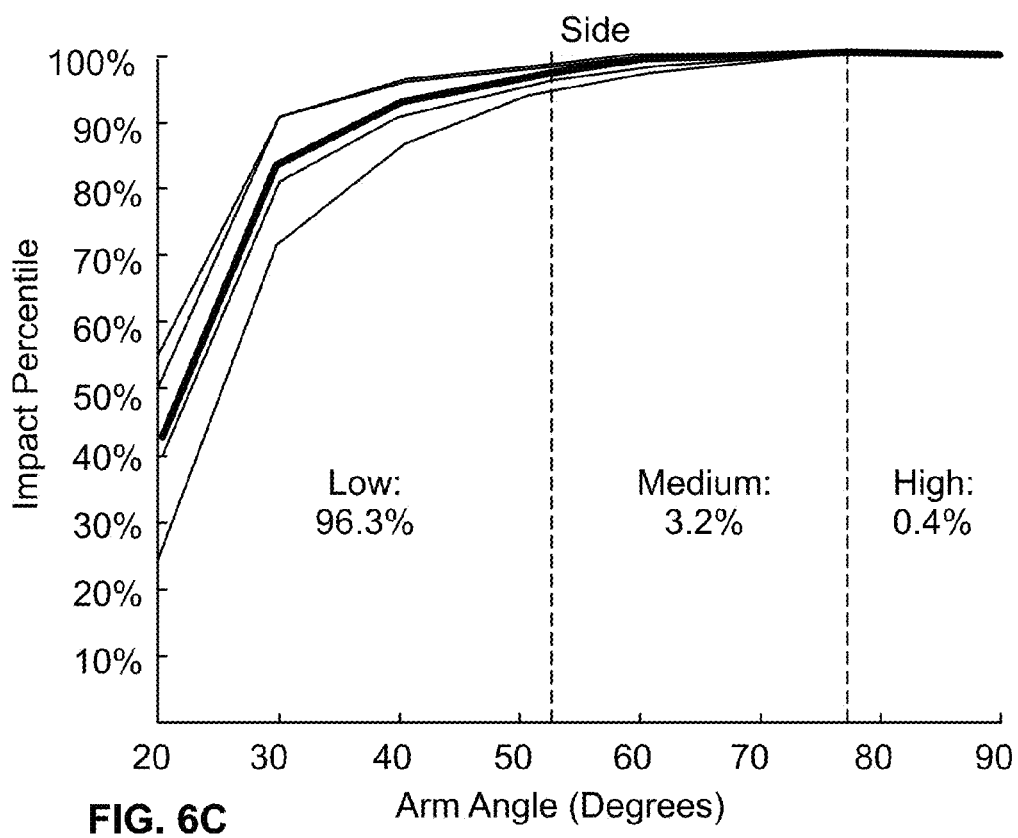
FIG. 6C
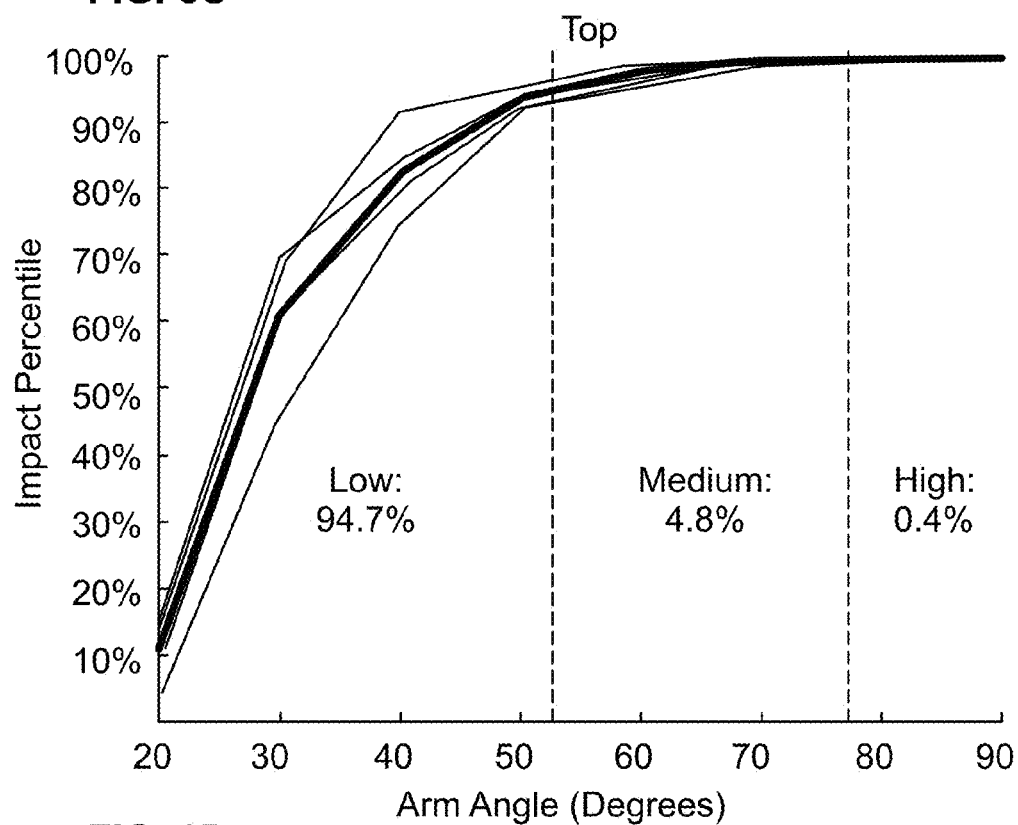
FIG. 6D
FIG. 6

METHODOLOGY FOR ASSESSING THE BIOMECHANICAL PERFORMANCE OF HELMETS

RELATED APPLICATIONS

This application claims the benefit of U.S. Provisional Application No. 62/027,492 filed Jul. 22, 2014 and herein incorporated by reference.

STATEMENT REGARDING FEDERALLY SPONSORED RESEARCH & DEVELOPMENT

Not applicable.

INCORPORATION BY REFERENCE OF MATERIAL SUBMITTED ON A COMPACT DISC

Not applicable.

BACKGROUND OF THE INVENTION

Optimizing the protective capabilities of helmets is one of several methods of reducing brain injury risk in sports. Football is often the focal point of concussion research because of its popularity and the high incidence of concussions associated with it. However, the rate of concussion is higher in ice hockey. Moreover, it is the most common injury for women's collegiate ice hockey, and the second most common for men's. The current helmet safety standards for hockey helmets have changed little over the past 50 years. The first hockey helmet standards were instituted by the Swedish Ice Hockey Association (SIA) in 1962. Shortly thereafter, US and Canadian organizations developed similar standards. Today, most hockey helmets bear stickers representing certification by 3 different organizations: the Hockey Equipment Certification Council (HECC), the Canadian Standards Association (CSA), and the International Organization for Standardization (ISO) represented by a CE marking. These standards all have similar pass/fail criteria that were implemented to reduce the risk of catastrophic head injuries.

Recently, concussion has gained national attention and become a research priority as the incidence of injury rises and concerns about the long-term effects of repeated mild injury are brought to light. Many strategies have been employed in attempts to decrease the incidence of concussion, such as rule changes, education programs, legislation, and improvements in protective equipment. Examples of rule changes designed to reduce injuries include fair-play and body-checking rules, which are implemented in some ice hockey leagues. Studies have shown a reduction in the incidence of more serious injuries including concussions when these rules are in place.

Education programs such as the Centers for Disease Control and Prevention's "HEADS UP" on concussion initiative and the Hockey Concussion Education Project (HCEP) were developed to help educate coaches, players, and their parents on preventing, identifying, and responding appropriately to concussions. Although most states in the US now have concussion laws in place, it is unclear at this time how effective they are. These laws usually focus on education, removal from play, and approval required for return to play.

There is currently no objective information available to consumers on which hockey helmets provide better protection against serious, as well as milder, head injuries like concussions. Prior to the development of the Football Summation of Tests for the Analysis of Risk (STAR) Evaluation System in 2011, this information was not available for football helmets either. Since the first set of helmet ratings using this evaluation system was released, the number of helmets receiving the highest rating possible of 5 stars has risen from just one to a total of 12 helmets in 2014. In the past, there were no conclusive studies on the effectiveness of different helmet types in reducing concussions on the field. However, recent research has demonstrated that the risk of concussion on the field is lowered with a helmet that better reduces head accelerations upon impact.

Football STAR was developed based on two fundamental principles. The first is that the tests performed are weighted based on how frequently a similar impact would occur on the field during one season of play. The second is that helmets that decrease acceleration decrease the risk of concussion. There are a number of concussion risk functions that have been developed to define probability of concussion as a function of linear head acceleration, angular head acceleration, or both. Debates over the mechanisms of brain injury and the ability of metrics that include linear or angular head acceleration to predict injury risk are long-standing.

Numerous studies have attempted to differentiate the effects of linear and angular head accelerations on brain injury and determine if one or the other is more likely to result in concussion. Current metrics for head injury safety standards use only linear head acceleration, and are based on human cadaver skull fracture and animal data. However, more recently it has been shown that the combination of linear and angular head acceleration is a good predictor of concussion, and that helmets reduce both linear and angular acceleration.

The Football STAR equation was developed to identify differences in the ability of football helmets to reduce concussion risk. The equation represents the predicted concussion incidence for a football player over one season. This predictive value is determined from laboratory tests with a helmeted headform to simulate head impacts at different locations and energy levels. Each laboratory condition is associated with the number of times that type of impact would occur over one season (exposure), and the probability that a concussion would occur due to the resultant head acceleration during each test (risk). In the Football STAR equation (Eq. 1), L represents the impact location of front, side, top, or back; H represents the drop height of 60, 48, 36, 24, or 12 in; E represents the exposure as a function of location and drop height, and R represents risk of concussion as a function of linear acceleration (a).

$$\text{Football STAR} = \sum_{L=1}^{4} \sum_{H=1}^{5} E(L, H) * R(a) \quad (1)$$

BRIEF SUMMARY OF THE INVENTION

In one embodiment, the present invention provides a new evaluation system for hockey helmets. The evaluation system provides a quantitative measure of the ability of individual helmets to reduce the risk of concussion. In a preferred embodiment, the Hockey STAR system provides test conditions weighted to represent how often hockey players experience similar impacts.

In another embodiment, present invention provides an evaluation approach that is the Summation of Tests for the Analysis of Risk (STAR) formula, which combines head impact exposure with brain injury probability over the broad range of 227 head impacts that a hockey player is likely to experience during one season. These impact exposure data may be mapped to parameters using a series of 12 impact conditions comprised of three energy levels and four head impact locations, which include centric and non-centric directions of force. Injury risk is determined using a multivariate injury risk function that incorporates both linear and rotational head acceleration measurements. The methodology provides a framework to optimize hockey helmet design for injury risk reduction, as well as providing meaningful metrics to assess the relative performance of hockey helmets.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

In still other embodiments, the present invention provides a novel methodology for comparing the performance of different hockey helmets. The methods include both linear and rotational acceleration. The exposure and testing conditions represent the number and type of head impacts experienced by hockey players. The biofidelity of the system was ensured by comparison with on-ice player data and other testing methods.

In other embodiments, the present invention provides an impact pendulum designed and built for laboratory testing.

It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

In the drawings, which are not necessarily drawn to scale, like numerals may describe substantially similar components throughout the several views. Like numerals having different letter suffixes may represent different instances of substantially similar components. The drawings illustrate generally, by way of example, but not by way of limitation, a detailed description of certain embodiments discussed in the present document.

FIG. 6A-6D. Impact energy CDFs for each impact location resulting from the transformation of on-ice data to laboratory impact conditions. The gray lines represent impact energy CDFs for each population and the black line is the equal-weight average of the four populations. The dashed lines show the bounds used to determine the percentage of impacts at each location associated with the low, medium, and high-energy impact conditions. This analysis was used to define the exposure weightings for each impact configuration in the Hockey STAR formula.

DETAILED DESCRIPTION OF THE INVENTION

Figure 1A:
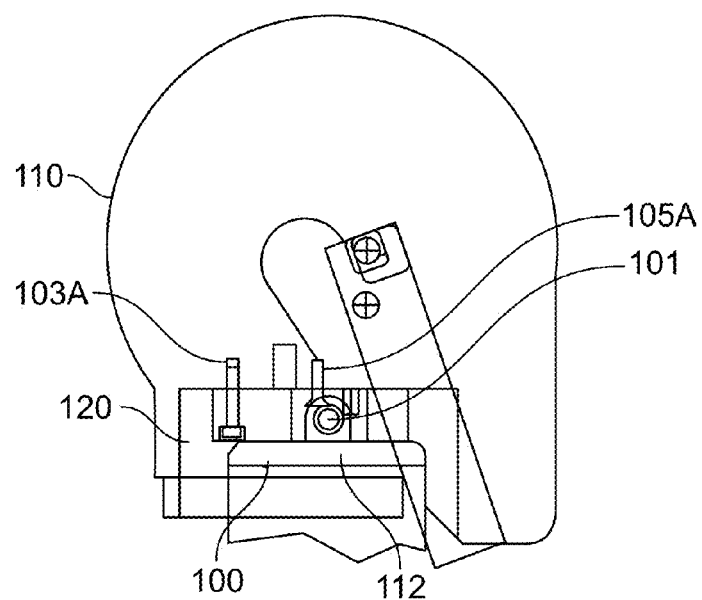
FIG. 1A illustrates a neck adapter for use with an embodiment of the present invention.

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a representative basis for teaching one skilled in the art to variously employ the present invention in virtually any appropriately detailed method, structure or system. Further, the terms and phrases used herein are not intended to be limiting, but rather to provide an understandable description of the invention.

The rating methodology of the present invention may be used with hockey helmets as well as any other head protection device. For illustrative purposes only, an embodiment concerning hockey helmets is described. The present invention improves upon the Football STAR methodology by incorporating several important modifications (Eq. 2). The risk function now incorporates both linear and rotational acceleration. In one embodiment of the Helmet STAR equation, L represents the head impact locations of front, side, top, or back; θ represents different impact energy levels defined by the angle of the pendulum arm used to impact the head; E represents exposure, or the number of times per season a player is expected to experience an impact similar to a particular testing condition as a function of location and impact energy; and R is the risk of concussion as a function of linear (a) and angular (α) head acceleration.

$$\text{Helmet Star} = \sum_{L=1}^{4} \sum_{\theta=1}^{3} E(L, \theta) * R(a, \alpha). \quad (2)$$

The risk function now incorporates both linear and rotational acceleration. In one embodiment of the Helmet STAR equation, L represents the head impact locations of front, side, top, or back; θ represents different impact energy levels defined by the angle of the pendulum arm used to impact the head; E represents exposure, or the number of times per season a player is expected to experience an impact similar to a particular testing condition as a function of location and impact energy; and R is the risk of concussion as a function of linear (a) and angular (α) head acceleration.

In another embodiment of the present invention, the testing matrix may include 3 impact energy levels and 4 impact locations, for a total of 12 testing conditions per helmet. In preferred embodiment, the testing methodology includes using two helmets of every model tested. Each of these helmets may be tested in the 12 conditions twice for a total of 48 tests per helmet model. The two acceleration values for each helmet's test conditions may be averaged for each impact condition prior to using the risk function to determine probability of concussion.

Concussion risks are multiplied by the exposure values for each impact condition to determine incidence values. All incidence values are aggregated to calculate a Hockey STAR value for each helmet. The Hockey STAR values for each helmet are averaged to determine a helmet model's overall Hockey STAR value.

Hockey Head Impact Exposure

In another embodiment of the present invention, head impact exposure may be defined as the number of impacts a player experiences over one season of play. Based on prior data, the median number of head impacts per player per season experienced by collegiate athletes was 287 for males and 170 for females. The median number of impacts per player per season for youth athletes was 223. The median values for each population were averaged to determine an overall exposure of 227 impacts. This value was used to represent the total number of impacts for one player over one season. The exposure value was further defined by impact location and severity as described below.

Data collected with the helmet-mounted accelerometer arrays was used to map on-ice player impact exposure to lab conditions. Data from two male and two female NCAA ice hockey teams as well as one male and one female high school team were included. The data were scaled to reduce measurement error using a relationship determined from correlating resultant head accelerations calculated from the helmet instrumentation to a reference measurement in an instrumented dummy headform during controlled laboratory impact tests.

The helmet data were then stratified by impact location. The locations are defined by the azimuth and elevation of the impact vector and are generalized into bins representing the front, right, left, back and top of the head. The front, right, left, and back consist of impacts with an elevation less than 65°, and are divided equally into 4 bins that are centered on the intersection of the midsagittal and coronal planes, but offset by 45°. The remaining impacts greater than 65° in elevation are grouped as top impacts. The exposure for each impact location was weighted by how often they occur in data collected in the literature. The front, side (left and right combined), and back were approximately 30% each, with the remaining 10% of impacts to the top of the head. These values were used to weight exposure by impact location.

Hockey Helmet Impact Device

Figure 1B:
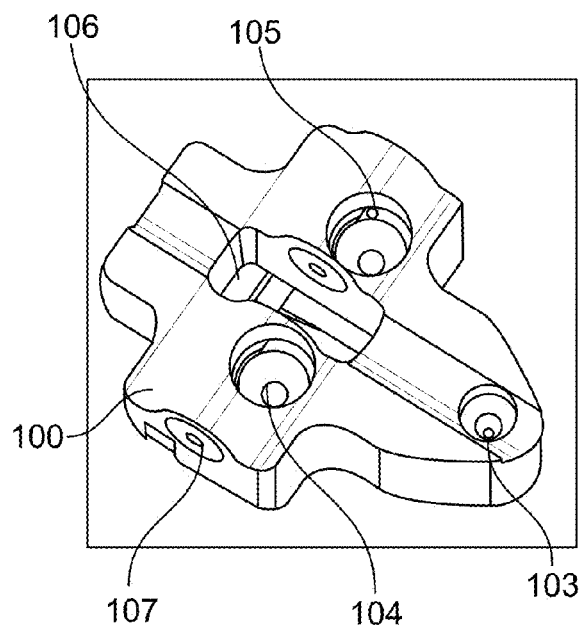
FIG. 1B illustrates a neck adapter installed in a headform for use with an embodiment of the present invention.
Figure 1C:
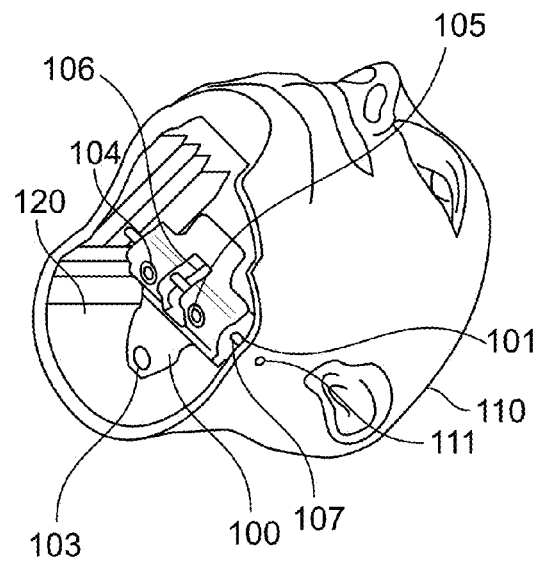
FIG. 1C is a cross sectional view showing a neck adapter installed in a headform for use with an embodiment of the present invention.

In a further embodiment, the present invention includes transforming on-ice player head acceleration data distributions to impact conditions in the lab. As shown in FIGS. 1A-1C, in another aspect, the present invention provides an adaptor plate 100 to mount a headform 110, which may be a NOCSAE headform, on a neck 112, which may be a Hyrbid III (not shown). Given the constraints of headform 110, adaptor plate 100 is unique in that it maximizes the anatomical accuracy of the location of the center of gravity of headform 110 relative to the occipital condyle pin 101 of neck 112. By allowing headform 110 to be mounted on a flexible neck, in a location that maintains biofidelity with an actual in use location, both linear and rotational head motion can occur during impact testing, which is predictive of real-world head injury. Existing headforms do not maintain biofidelity and do not properly locate the center of gravity. As a result, the prior designs are unable to obtain accurate rotational measurements, which commonly locate the neck rearward in headform 110.

Figures 2A, 2B:
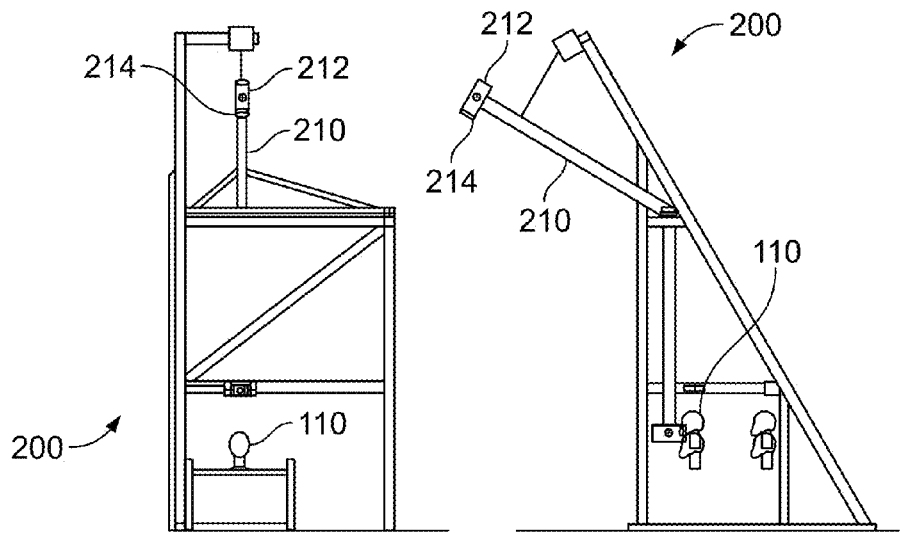
FIGS. 2A-2D. The custom impact pendulum device was used to strike a NOCSAE headform mounted on a Hybrid III 50th percentile neck. The head and neck were mounted on a sliding mass that simulates the effective mass of the torso during impact. The slide table has 5 degrees of freedom so that any location on the helmet could be impacted: translation along the x axis, translation along the y axis, translation along the z axis, rotation about the y axis, and rotation about the z axis.
Figure 2C:
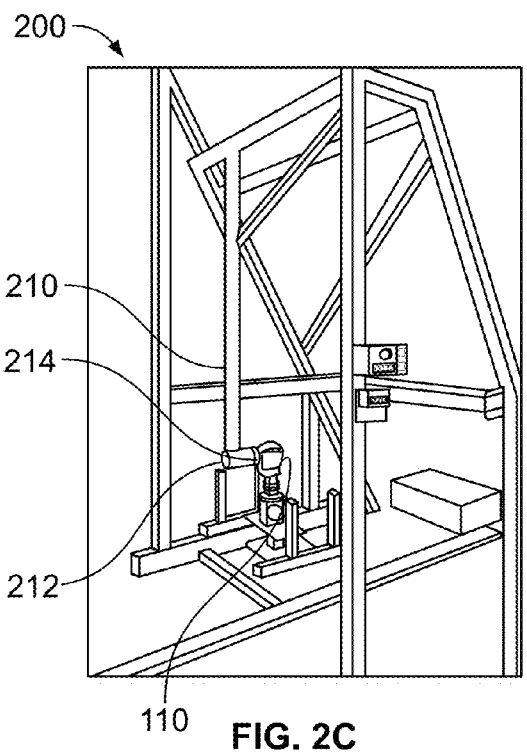
Figure 2D:
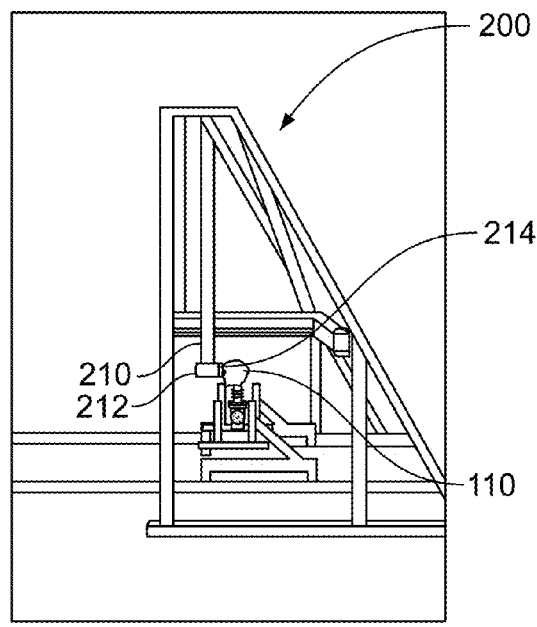
Figure 3A:
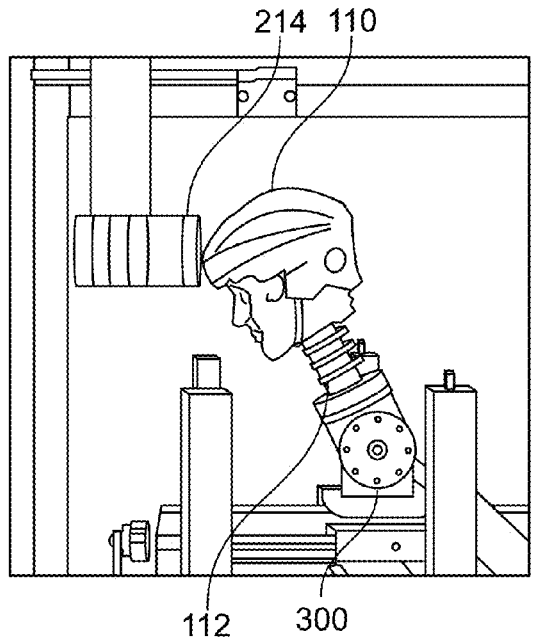
FIGS. 3A-3D. Depict front (3A), side (3B), back (3C), and top (3D) impact locations used to assess helmet performance. The side and top impact locations are non-centric, meaning the direction of force is not aligned with the center of gravity of the headform; while the front and back impact locations are centric.
Figure 3B:
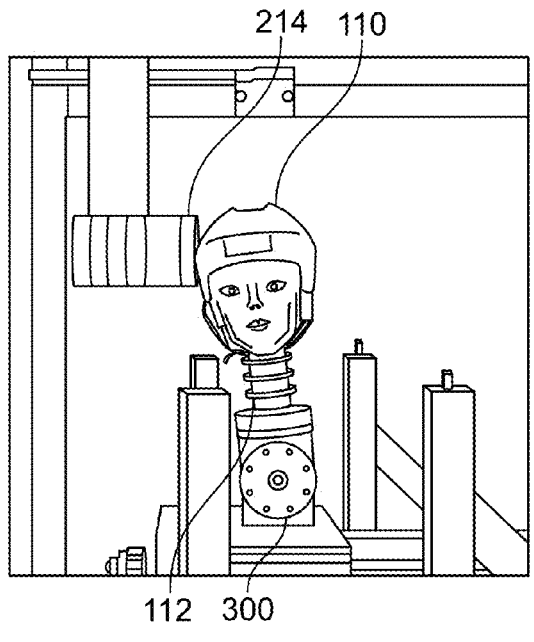
Figure 3C:
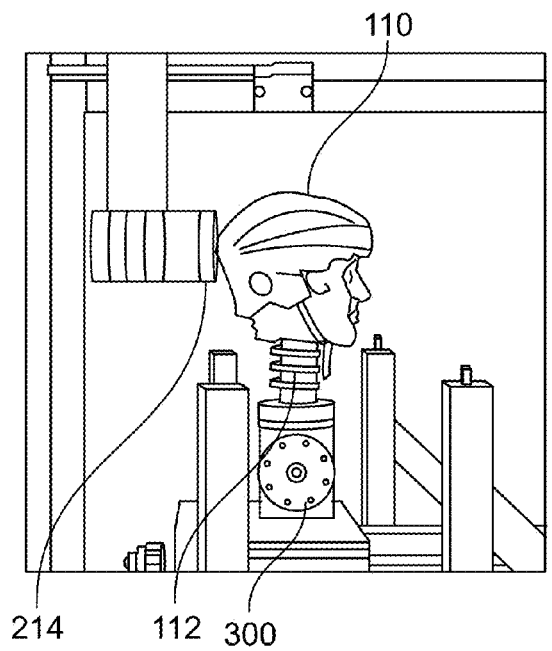
Figure 3D:
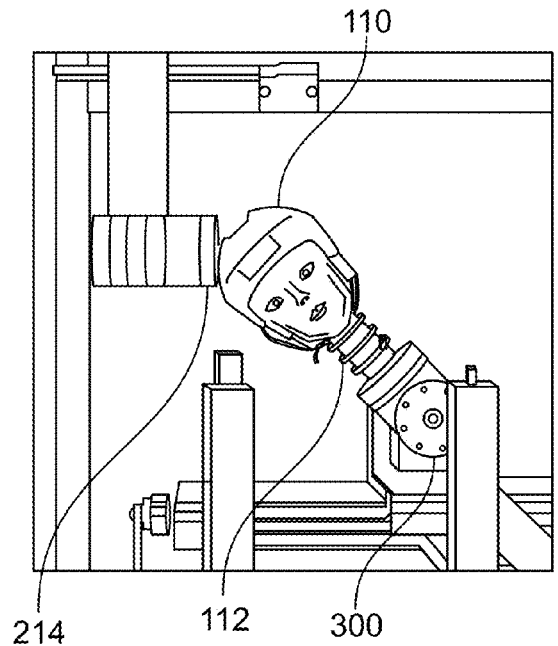

In a particular embodiment, adapter 100 and headform 110 are adapted and configured to allow for mounting in a position and location, when used with the force producing apparatus 200 shown in FIG. 2, that maintains biofidelity with a real-life application. Adapter 100 includes one or more mounting holes 103-105, which receive fasteners such as 103A and 105A, to secure adapter 100 to headform 110. Opening 106 is also provided to receive neck 112. Bore 107 in adapter 100 and opening 111 in headform 110 are sized to receive pin 101. When adapter 100 is located in opening 120 of headform 110, the above described openings and fasteners properly locate headform in a position that replicates a real-life application. As stated above, the configuration results in locating the center of gravity of headform 110 relative to the occipital condyle pin 101 of neck 112 when headform 110 is subjected to pendulum impact test apparatus 200 that is capable of emulating head impacts that occur during participation in sports.

In another embodiment, the present invention provides a force producing apparatus 200. In a preferred embodiment, the force producing apparatus is an impact pendulum that is specifically designed to be a repeatable and reliable testing device.

Impact pendulum 200 is designed to evaluate the ability of sport helmets to reduce risk of concussion, skull fracture, and more severe brain injury. Impact pendulum 200 includes movable arm 210 that can generate linear and rotational headform accelerations that mimic those experienced by athletes. Impactor 212 provides an impacting mass that is adjustable to emulate the full range of head impact characteristics experienced by athletes. Furthermore, impact pendulum 200 is repeatable over this full range of possible head impact configurations. This embodiment may be used to improve helmet design in efforts to reduce the number of head injuries in sports.

In other embodiments, the present invention provides a series of impact tests were performed over a range of input energies using impact pendulum 200 to map laboratory-generated head accelerations to those measured on-ice directly from hockey players.

In a preferred embodiment, pendulum 200 may be used since it provides increased repeatability and reproducibility when compared with other head impact methods. Pendulum arm 210 may be composed of 10.16×5.08 cm rectangular aluminum tubing with a 16.3 kg impacting mass at its end. The length of pendulum arm 210 from the center of its pivot point to the center of its impacting mass may be 190.5 cm. The pendulum arm may have a total mass of 36.3 kg and a moment of inertia of 72 kg m$^2$. The impacting mass accounts for 78% of the total moment of inertia. Nylon impactor face 214 may have a diameter of 12.7 cm, which is flat and rigid in an effort to maximize repeatability and reproducibility of the tests. Furthermore, a rigid impacting face was chosen due to rigid surfaces in hockey, and to avoid impactor compliancy masking differences between helmets in comparative testing.

The pendulum impactor 212 strikes headform 110, which may be a medium NOC-SAE that is mounted on neck 112. Neck 112 may be a Hybrid III 50th percentile neck. In a further preferred embodiment, the headform may be modified to provide the most realistic fit between helmet and headform. Adaptor plate 100 is used to mate the headform 110 to neck 112 while keeping the relative locations of the occipital condyle pin and headform center of gravity (CG) as close as possible to that of the Hybrid III 50th percentile male head and neck assembly or any other desired target category. Material may need to be removed from the underside of the headform to optimize the position of the occipital condyle and accommodate the neck. The adaptor plate's mass may also need to be equal to the material removed.

As shown in FIGS. 3A-3D, the head and neck assembly are mounted on a sliding mass 300 intended to simulate the effective mass of the torso during impact. This sliding mass is part of a commercially available linear slide table that is commonly used for helmet impact testing (Biokinetics, Ottawa, Ontario, Canada). Contrary to most helmet drop test rigs, the system of the present invention allows for linear and rotational motion to be generated during impact. To measure the kinematics resulting from impact, headform 110 was instrumented with a 6 degrees of freedom sensor package consisting of 3 accelerometers and 3 angular rate sensors (6DX-Pro, DTS, Seal Beach, Calif.).

The front, side, back, and top of the headform were chosen to impact in laboratory tests. In order to account for a wider array of impact types, two of the locations were centric, or aligned with the CG of the headform (front and back), and two were non-centric (side and top). These locations resulted in some impacts with higher rotational components for a given linear acceleration than others, which were quantified by the effective radius of rotation at each condition. Effective radius of rotation was defined as the quotient of peak linear acceleration and peak rotational acceleration. Table 1 specifies the impact locations using measurement markings provided on the commercially available linear slide table.

TABLE 1

Measurement markings and angles of rotation on the linear slide table for each impact location tested.

|  | Y translation (cm) | Z translation (cm) | Y rotation (°) | Z rotation (°) |
| --- | --- | --- | --- | --- |
| Front | 40.3 | 8.9 | 25 | 0 |
| Side | 36.9 | 3.5 | 5 | 80 |
| Top | 42.7 | 13.5 | 40 | 90 |
| Back | 40.3 | 4.9 | 0 | 180 |

Mapping Exposure Data to Laboratory System

A series of tests were performed to map the on-ice helmet data to pendulum impacts. For these tests, the NOCSAE headform was fitted with a size medium CCM Vector V08 helmet (Reebok-CCM Hockey, Inc., Montreal, Canada). The V08 model was chosen because it was one of the helmet types worn by instrumented players to generate head impact exposure data. The linear acceleration and angular rate data were collected at a sampling rate of 20,000 Hz. Linear acceleration data were filtered to CFC 1000 Hz according to SAE J211, while angular rate data were filtered to CFC 155. Angular acceleration was calculated by differentiating the angular rate data. All data were then transformed to the CG of the headform. Three V08 helmets were tested, with each impacted from pendulum arm angles of 20°, 30°, 40°, 50°, 60°, 70°, 80°, and 90° at each of the four locations defined above, resulting in 96 impact tests.

After determining the total impact exposure per player per season and stratifying the on-ice helmet data by impact location, the data were transformed to laboratory impact conditions. To do this, the on-ice data for each location were reduced to include only impacts with effective radii of rotation in the range of corresponding laboratory impacts. Within these constraints, the on-ice head acceleration distributions were related to impact conditions in the lab. Bivariate empirical cumulative distribution functions (CDF) comprised of peak linear and peak rotational head accelerations were computed for on-ice data within each impact location's constraints. The CDFs were defined by determining the percentage of impacts less than or equal to each impact's peak linear and peak rotational acceleration. Using the location-specific CDFs, the percentile impact for each pendulum impact energy was determined by relating peak linear and peak rotational acceleration average values generated from each laboratory condition. Through this process, location-specific impact energy CDFs were determined for each population (male collegiate, female collegiate, male high school, and female high school). The 4 resulting impact energy CDFs were then averaged for equal weighting between populations.

Low, medium, and high impact energy conditions were set prior to computing the weighting used in the Hockey STAR formula. These conditions were chosen to be representative of a span of impacts severities that encompass both sub-concussive and concussive head impacts, and are defined by pendulum arm angles of 40° (low), 65° (medium), and 90° (high). Weightings to be used for the Hockey STAR test configurations were determined by setting bounds on the impact energy CDFs midway between each test angle. For each location, the percentage of impacts below 52.5° was defined as the low energy condition, the percentage of impacts between 52.5° and 77.5° was defined as medium energy condition, and the percentage of impacts greater than 77.5° was defined as the high-energy condition. The weightings for each test configuration were then computed by multiplying these percentages by the total number of head impacts that the average hockey player sustains at each location.

Injury Risk Function

In yet another embodiment, the risk function used incorporates both linear (a) and angular (α) head acceleration components:

$$R(a,\alpha)=1/1+e^{-(-10.2+0.0433*a+0.000873*\alpha-0.000000920*a\alpha)} \quad \text{(Eq. 3)}$$

Figure 4:
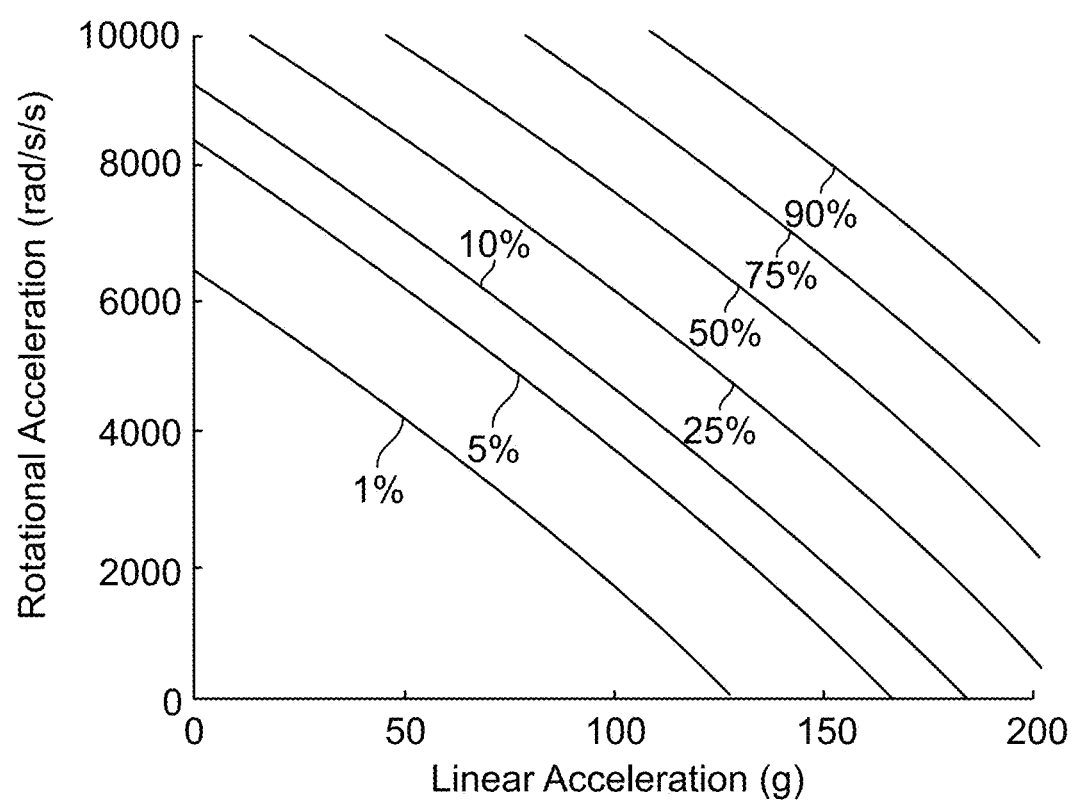
FIG. 4 shows concussion risk contours generated from linear and rotational accelerations.
Figure 5A:
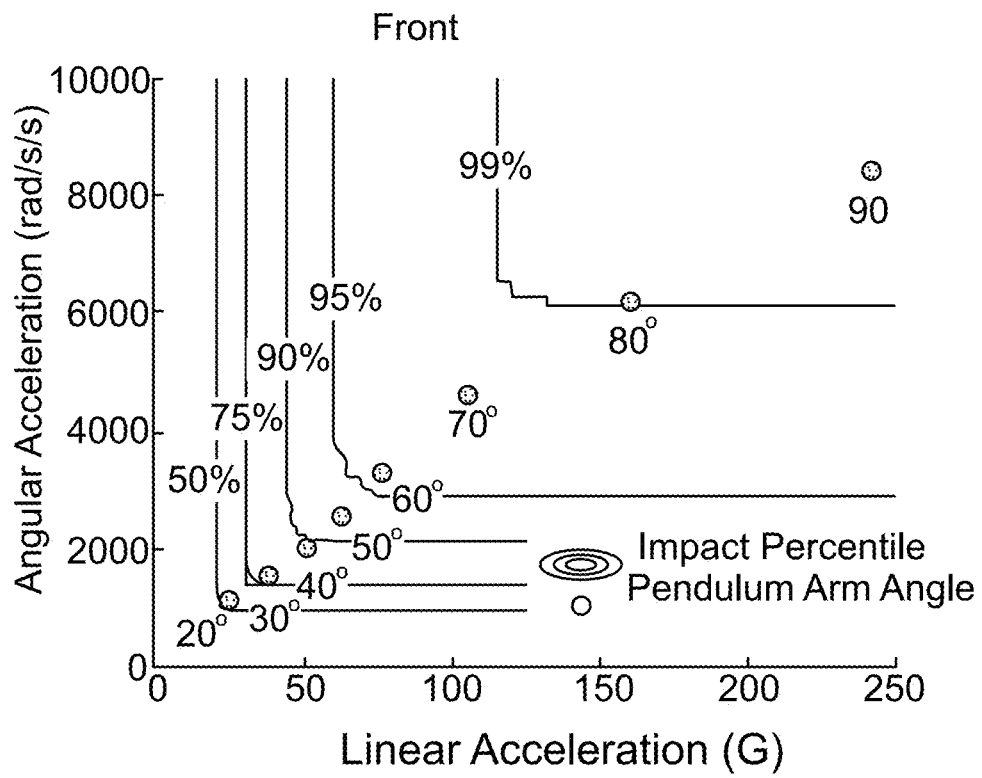
FIG. 5A-5D. Peak linear and rotational head acceleration values generated during the pendulum tests are overlaid on the bivariate CDFs for each impact location. These plots relate laboratory impact energies to on-ice head impact data and were used to define head impact distributions as a function of impact energy. Where a given impact energy (pendulum arm angle) fell within the distributions varied by impact location.
Figure 5B:
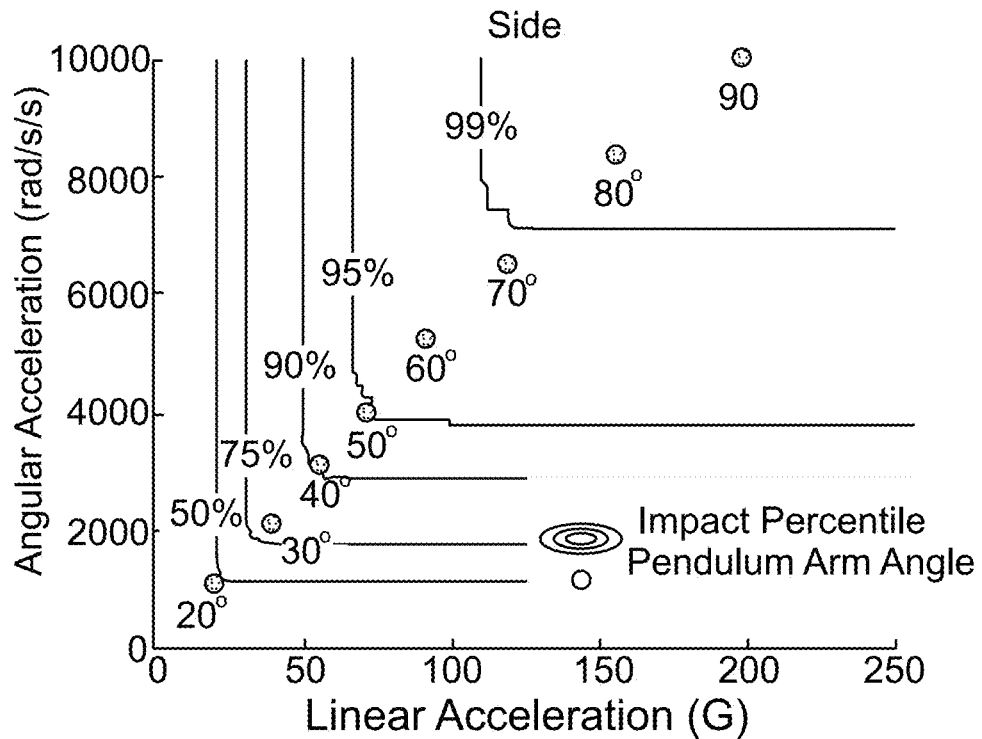
Figure 5C:
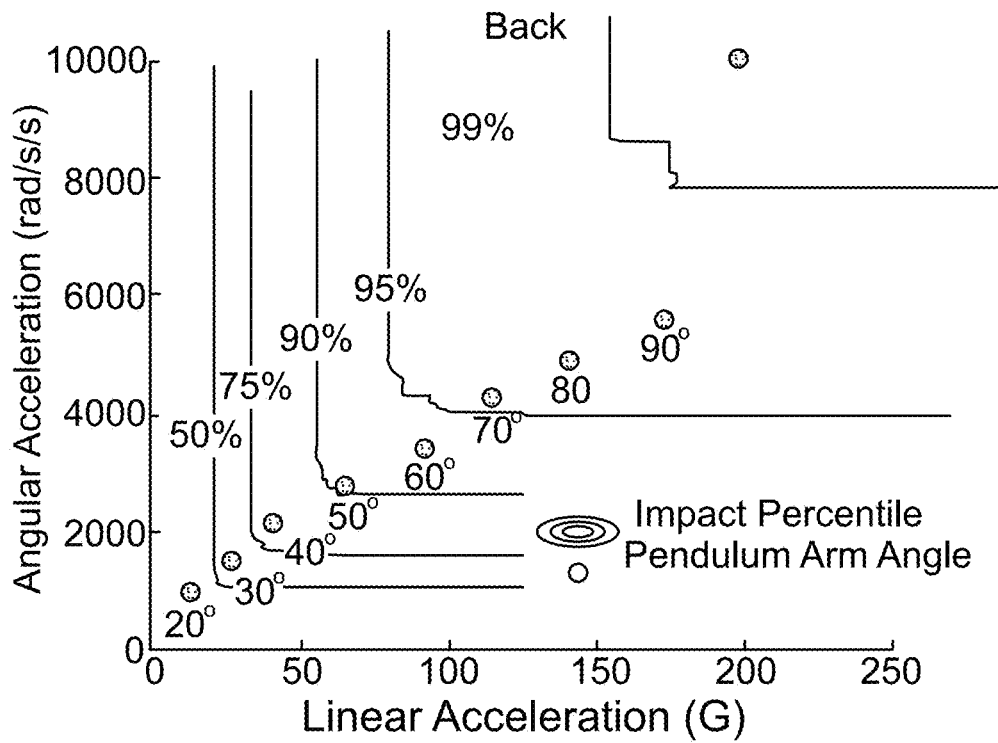
Figure 5D:
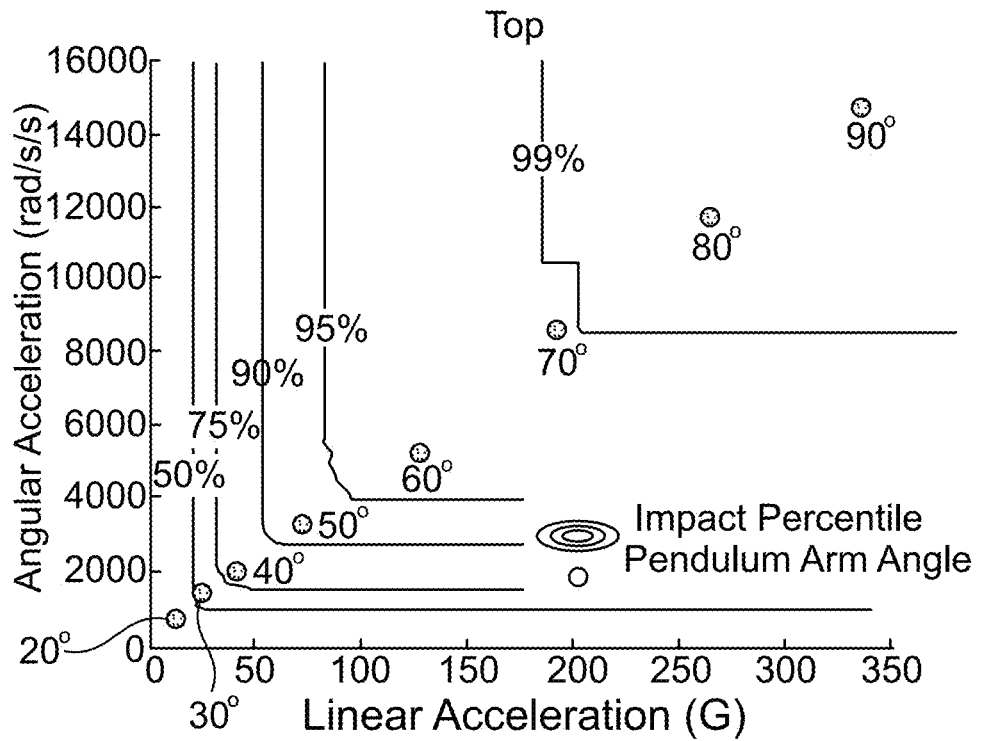

FIG. 4 shows concussion risk contours generated from linear and rotational accelerations. The risk function was developed using data collected from high school and collegiate football players. A multivariate logistic regression analysis was used to model risk as a function of linear and rotational head acceleration. There is an interaction term because linear and rotational acceleration are correlated. This risk function is unique in that it accounts for the under-reporting of concussion in the underlying data used to develop the curve. The predictive capability of the risk function was found to be good using NFL head impact reconstructions in addition to the impacts used to generate the function.

Exemplar Hockey Helmet Tests

Three exemplar helmets were used to demonstrate the Hockey STAR system of the present invention. Each helmet may be tested in 12 impact conditions: 4 locations with 3 impact energies per location. Pendulum arm angles of 40°, 65°, and 90° were tested, which equate to impact velocity of 3, 4.6, and 6.1 m/s. These illustrative tests differ from actual Hockey STAR tests in that only one helmet per model was tested, and each test configuration was only tested once. In other embodiments, each test condition may be tested twice for each helmet, and acceleration values in each condition may be averaged before calculating risk. Hockey STAR values for the two helmets of each model are averaged to determine a helmet model's overall Hockey STAR value. For demonstrative purposes, two hockey helmets and one football helmet were tested under these conditions and Hockey STAR values calculated.

Results

Mapping Exposure Data to Laboratory System

Bivariate CDFs for linear and rotational accelerations experienced by male collegiate hockey players are shown in FIG. 5 for each impact location. Peak linear and rotational head acceleration values generated during the pendulum tests are overlaid on the CDFs to illustrate how the laboratory tests relate to the on-ice head impact distributions. Constant impact energies varied in percentile by impact location. For example, releasing the pendulum arm from 40° was representative of the 88.2 percentile impact to the front location, 90.4 percentile impact to the side location, 81.4 percentile impact to the back location, and 80.7 percentile impact to the top location. This demonstrates that higher head accelerations were more commonly associated with back and top impact locations in the on-ice helmet data. The tails of these right-skewed distributions exhibited similar trends. Releasing the pendulum arm from 70° was representative of the 98.2 percentile impact to the front location, 98.6 percentile impact to the side location, 95.5 percentile impact to the back location, and 98.9 percentile impact to the top location.

Figure 6A:
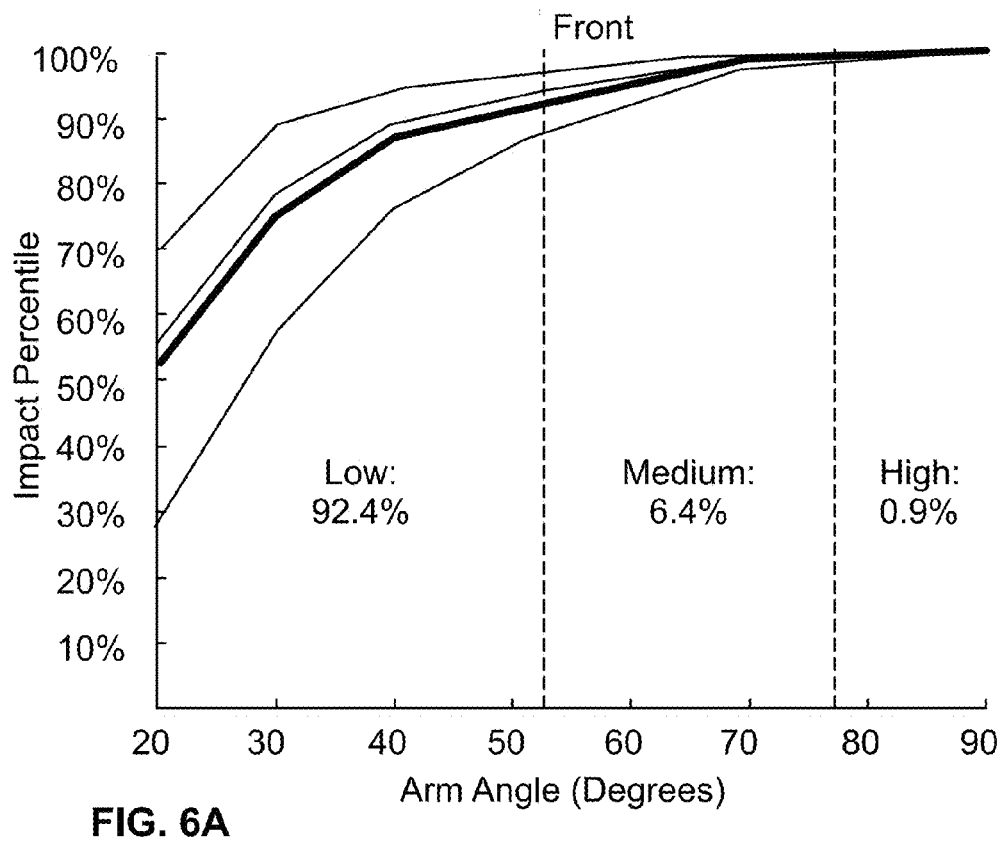
Figure 6B:
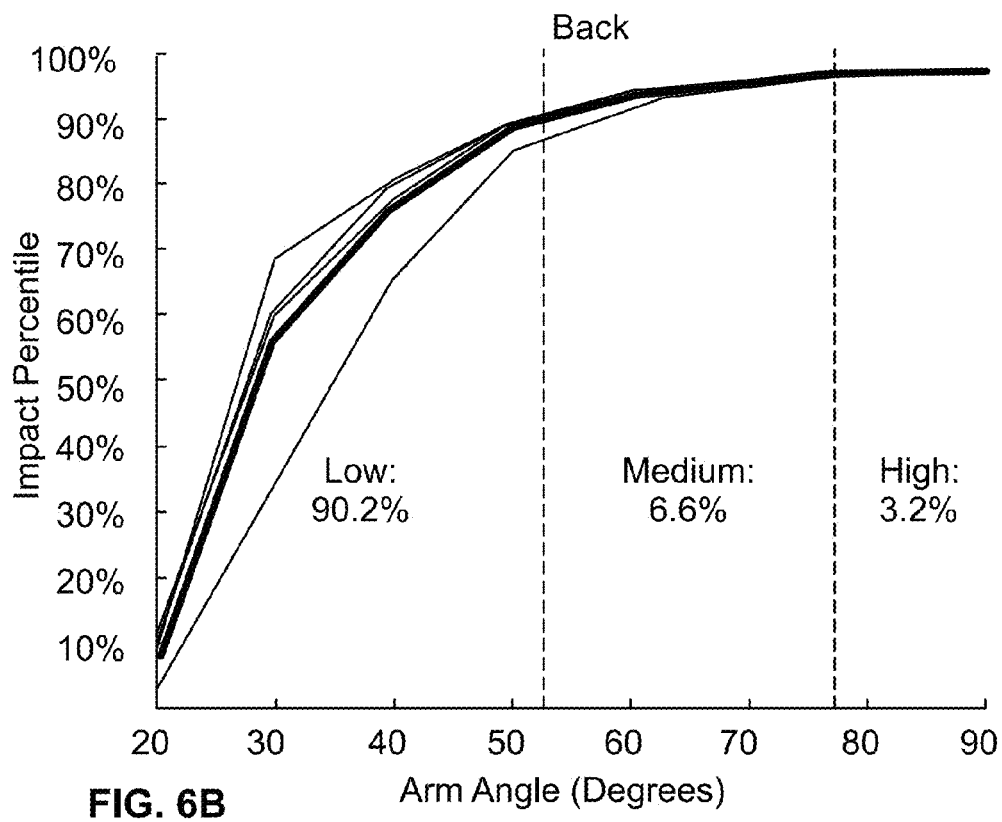
Figure 7A:
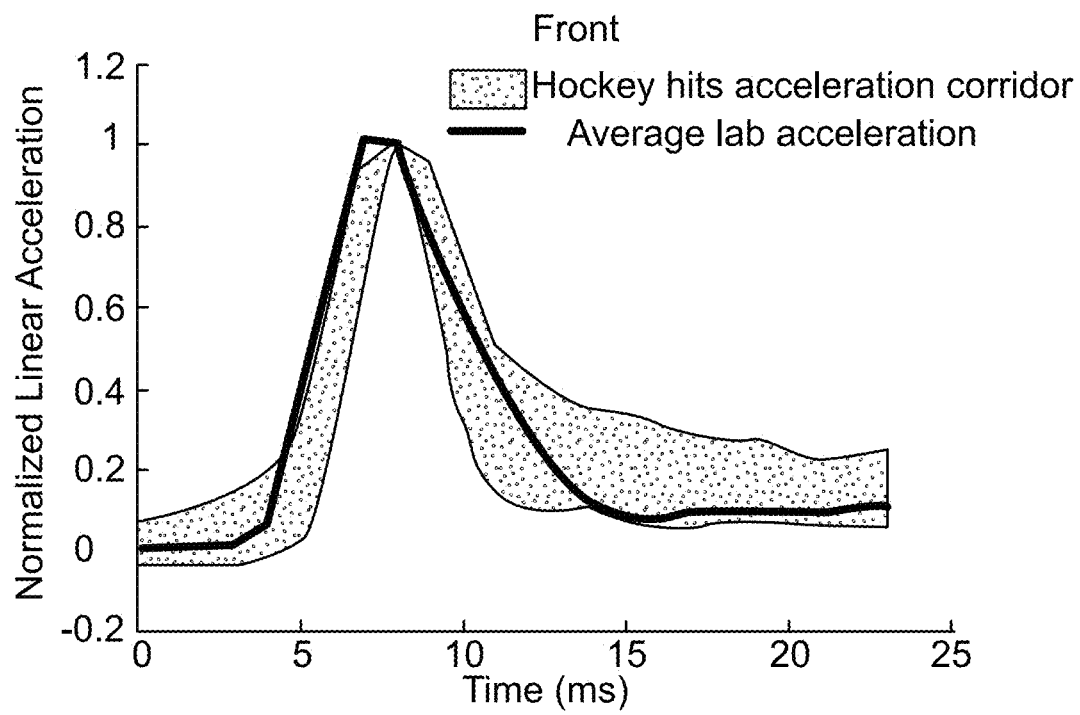
FIG. 7A-7D. Average acceleration traces from the laboratory pendulum tests were compared to corridors developed from on-ice volunteer data by impact location. The head impact response of the laboratory tests closely matches that which was measured directly from hockey players, suggesting the impact system generates a biofidelic response.
Figure 7B:
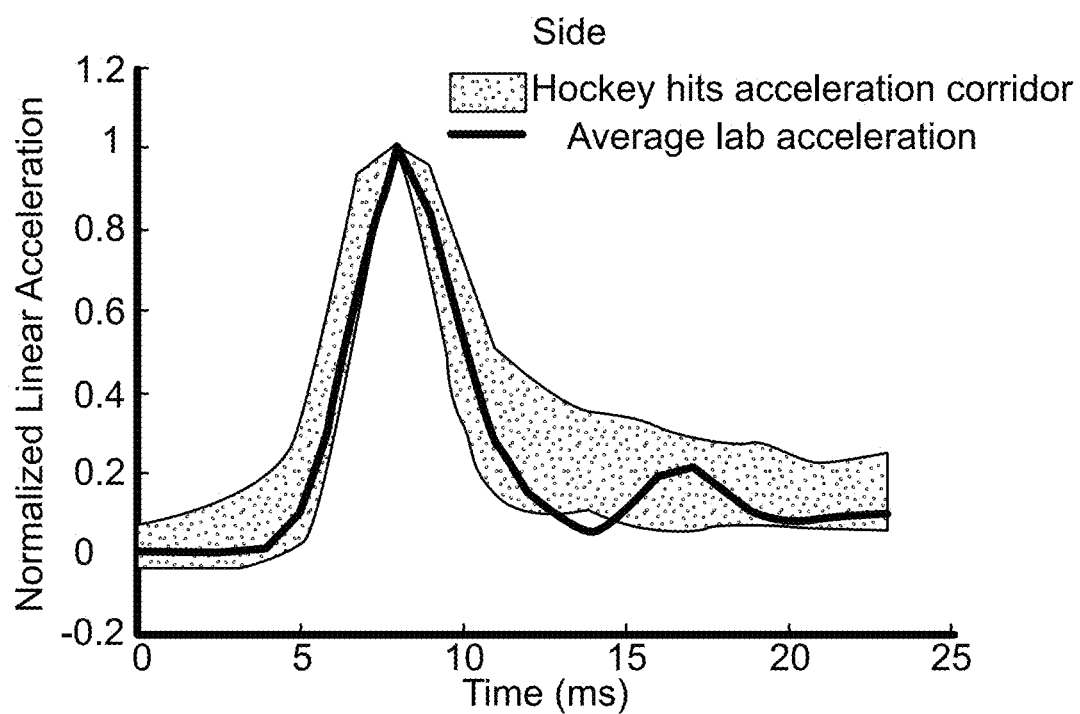
Figure 7C:
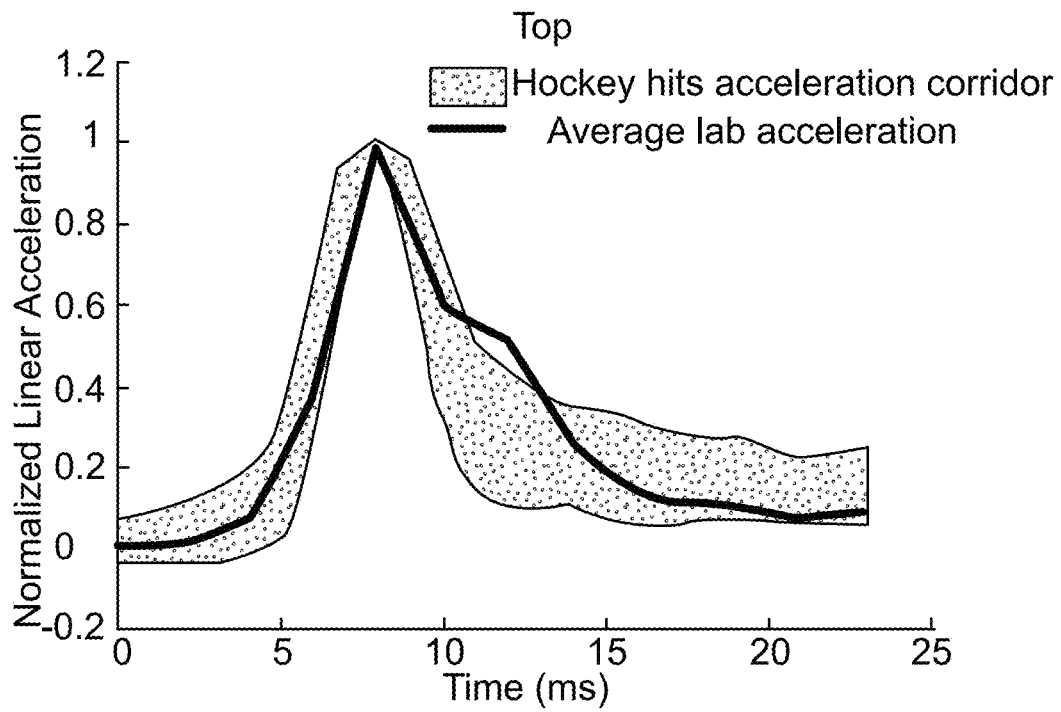
Figure 7D:
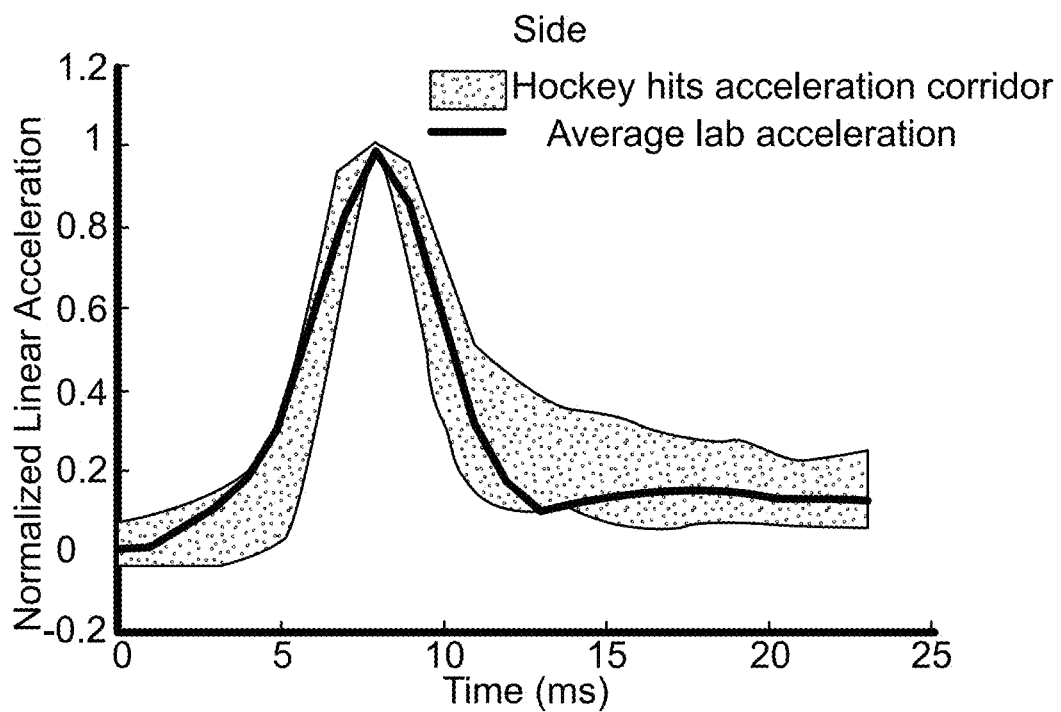
Figure 8A:
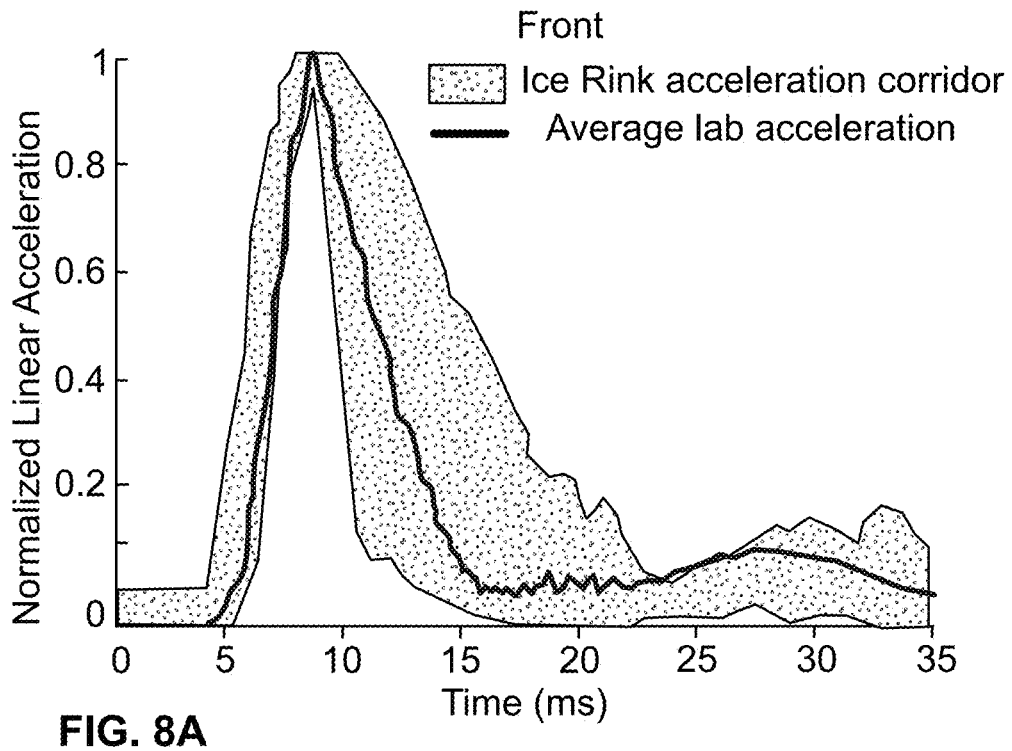
FIG. 8A-8D. Head impact responses generated in the lab were also compared to dummy head impacts collected at an ice rink. Here, average acceleration traces from the laboratory pendulum tests were compared to corridors developed from controlled dummy head impacts to the boards, glass, and ice at an ice rink. The head impact response of the laboratory tests closely matches that which was measured at the ice rink, which further suggests that impact system generates a biofidelic response.
Figure 8B:
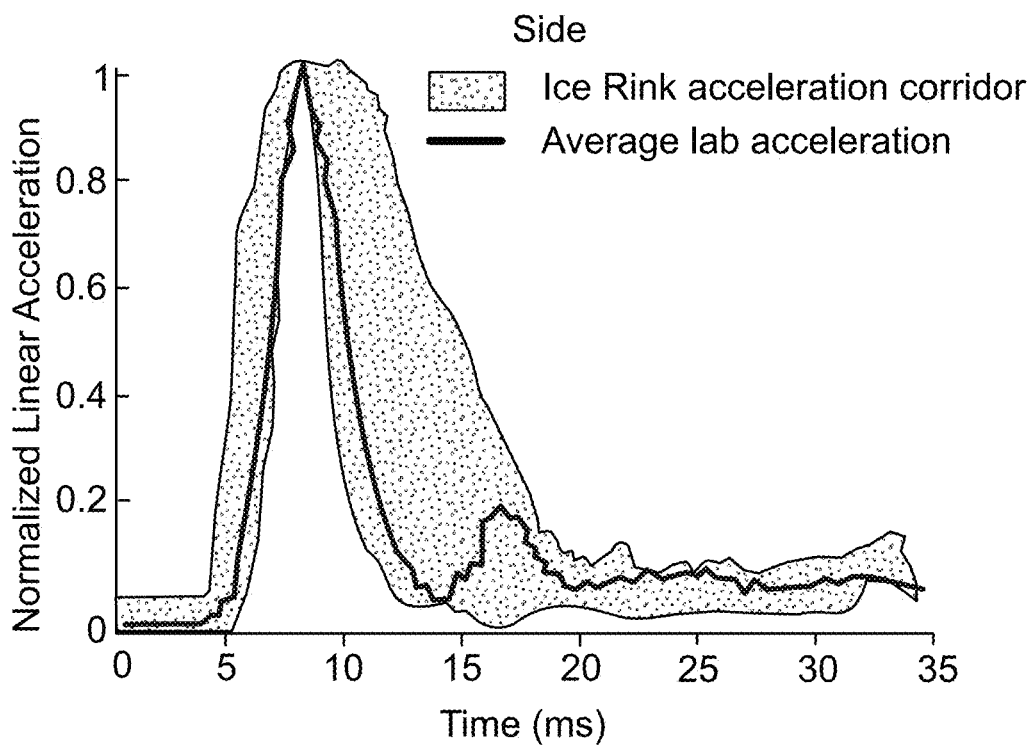
Figure 8C:
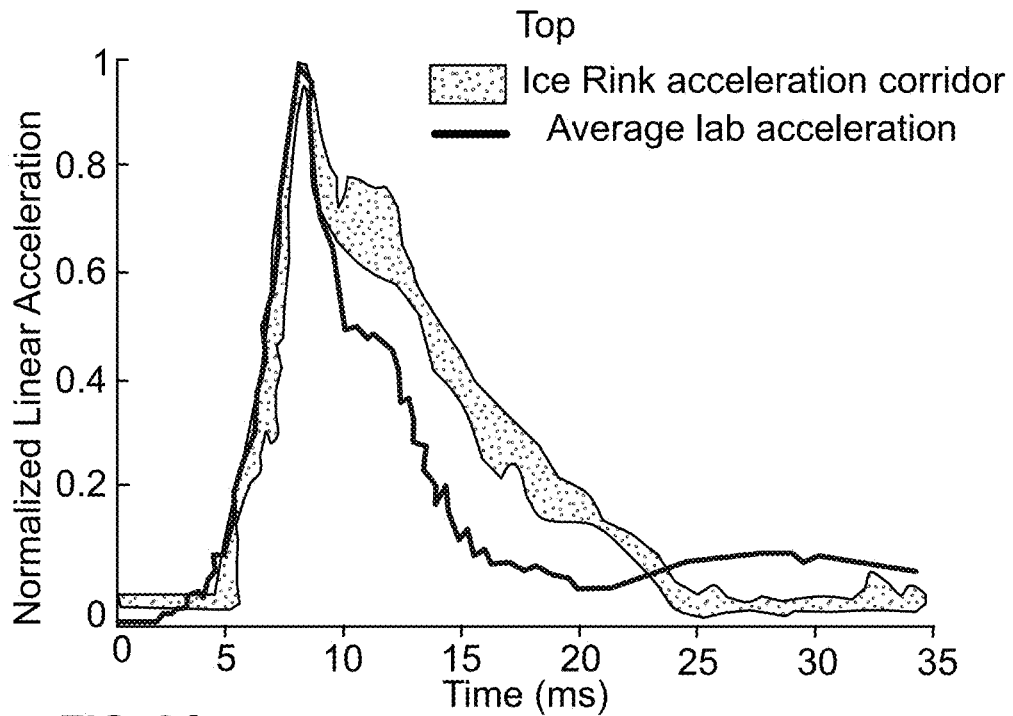
Figure 8D:
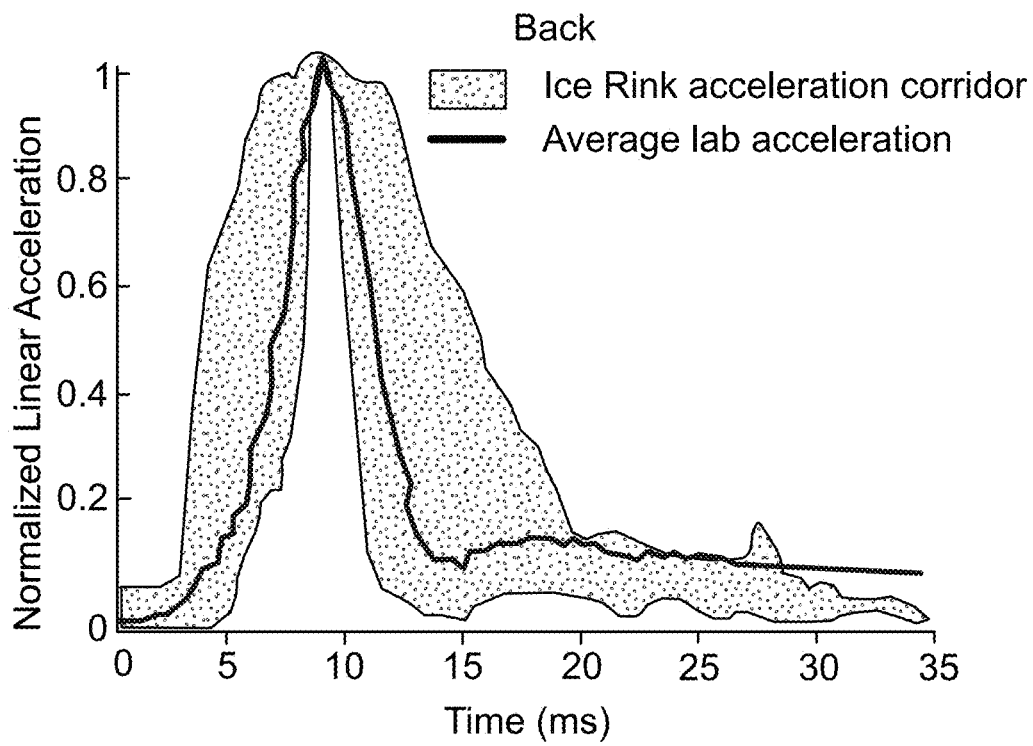

On-ice head acceleration distributions were transformed to impact energy distributions (represented by pendulum arm angle) by determining the percentage of on-ice data that fell below each energy for each impact location. This process was done for each population (male and female collegiate, male and female high school). Resulting impact energy CDFs were then averaged to determine an overall impact energy CDF that gave equal weighting to each population (FIG. 6). The impact energy CDFs were related to generalized impact energy conditions: a low energy condition (40° pendulum arm angle), a medium energy condition (65° pendulum arm angle), and a high-energy condition (90° pendulum arm angle). For all locations, the low energy condition accounts for greater than 90% of head impacts. The medium energy condition ranged between 3.2 and 6.8% of impacts for each condition. The high-energy condition generally accounted for less than 1% of impacts for each location, with the exception of the back location.

From this analysis, weightings were determined for each laboratory impact condition based on how frequently a player might sustain a similar impact (Table 2). Summating these laboratory condition-specific exposure values results in the 227 head impacts that the average player experiences throughout a season of hockey.

TABLE 2

Mapping of on-ice head impact exposure to generalized laboratory test conditions.

|  | 40° | 65° | 90° | Total |
|---|---|---|---|---|
| Front | 62.9 | 4.6 | 0.6 | 68.1 |
| Side | 65.6 | 2.2 | 0.3 | 68.1 |
| Top | 21.5 | 1.1 | 0.1 | 22.7 |
| Back | 61.4 | 4.5 | 2.2 | 68.1 |
| Total | 211.4 | 12.4 | 3.2 | 227 |

Each impact configuration was related to a number of impacts that the average player experiences during a season of play. These numbers represent the exposure weightings for each test condition in the Hockey STAR formula.

Exemplar Hockey Helmet Tests

Three helmets were evaluated with the Hockey STAR evaluation methods described above: two hockey helmets and one football helmet. The detailed results for each helmet are shown in Tables 3, 4, and 5.

TABLE 3

Hockey STAR evaluation of hockey helmet A with resultant peak linear (a) and angular (α) acceleration, corresponding risk of injury, and season exposure for each condition to calculate incidence.

| Impact location | Angle (°) | Peak a (g) | Peak α (rad/s²) | Risk of injury (%) | Exposure per season | Incidence per season |
|---|---|---|---|---|---|---|
| Front | 40 | 64 | 2154 | 0.34 | 62.9 | 0.213 |
| Front | 65 | 108 | 3591 | 5.94 | 4.6 | 0.273 |
| Front | 90 | 168 | 6680 | 86.57 | 0.6 | 0.519 |
| Side | 40 | 71 | 4220 | 2.39 | 65.6 | 1.568 |
| Side | 65 | 124 | 7149 | 64.74 | 2.2 | 1.424 |
| Side | 90 | 176 | 9370 | 98.34 | 0.3 | 0.295 |
| Top | 40 | 37 | 2590 | 0.16 | 21.5 | 0.035 |
| Top | 65 | 103 | 6061 | 26.23 | 1.1 | 0.289 |
| Top | 90 | 263 | 12,666 | 99.99 | 0.1 | 0.100 |
| Back | 40 | 41 | 2020 | 0.12 | 61.4 | 0.072 |
| Back | 65 | 111 | 4345 | 11.43 | 4.5 | 0.514 |
| Back | 90 | 169 | 6076 | 81.60 | 2.2 | 1.795 |
|  |  |  |  |  | STAR | 7.098 |

The resulting Hockey STAR value is 7.098.

TABLE 4

Hockey STAR evaluation of hockey helmet B with resultant peak linear (a) and angular (α) acceleration, corresponding risk of injury, and season exposure for each condition to calculate incidence.

| Impact location | Angle (°) | Peak a (g) | Peak α (rad/s²) | Risk of injury (%) | Exposure per season | Incidence per season |
|---|---|---|---|---|---|---|
| Front | 40 | 64 | 2570 | 0.48 | 62.9 | 0.299 |
| Front | 65 | 87 | 3819 | 3.21 | 4.6 | 0.148 |
| Front | 90 | 164 | 6333 | 81.58 | 0.6 | 0.489 |
| Side | 40 | 74 | 5037 | 5.04 | 65.6 | 3.305 |
| Side | 65 | 115 | 8254 | 75.17 | 2.2 | 1.654 |
| Side | 90 | 155 | 10,189 | 98.12 | 0.3 | 0.294 |
| Top | 40 | 66 | 3869 | 1.47 | 21.5 | 0.315 |
| Top | 65 | 124 | 7001 | 61.60 | 1.1 | 0.678 |
| Top | 90 | 163 | 9548 | 97.72 | 0.1 | 0.098 |

TABLE 4-continued

Hockey STAR evaluation of hockey helmet B with resultant peak linear (a) and angular (a) acceleration, corresponding risk of injury, and season exposure for each condition to calculate incidence.

| Impact location | Angle (°) | Peak a (g) | Peak a (rad/s$^2$) | Risk of injury (%) | Exposure per season | Incidence per season |
|---|---|---|---|---|---|---|
| Back | 40 | 56 | 3448 | 0.71 | 61.4 | 0.435 |
| Back | 65 | 135 | 6647 | 65.27 | 4.5 | 2.937 |
| Back | 90 | 178 | 9073 | 98.07 | 2.2 | 2.158 |
| | | | | | STAR | 12.809 |

The resulting Hockey STAR value is 12.809.

TABLE 5

Hockey STAR evaluation of a football helmet with resultant peak linear (a) and angular (a) acceleration, corresponding risk of injury, and season exposure for each condition to calculate incidence.

| Impact Location | Angle (°) | Peak a (g) | Peak a (rad/s$^2$) | Risk of injury (%) | Exposure per season | Incidence per season |
|---|---|---|---|---|---|---|
| Front | 40 | 37 | 1787 | 0.08 | 62.9 | 0.052 |
| Front | 65 | 76 | 2679 | 0.84 | 4.6 | 0.039 |
| Front | 90 | 115 | 3646 | 8.21 | 0.6 | 0.049 |
| Side | 40 | 35 | 2210 | 0.11 | 65.6 | 0.072 |
| Side | 65 | 64 | 3940 | 1.47 | 2.2 | 0.032 |
| Side | 90 | 122 | 7120 | 61.95 | 0.3 | 0.186 |
| Top | 40 | 32 | 1965 | 0.08 | 21.5 | 0.017 |
| Top | 65 | 67 | 3554 | 1.20 | 1.1 | 0.013 |
| Top | 90 | 100 | 4622 | 9.28 | 0.1 | 0.009 |
| Back | 40 | 44 | 2177 | 0.16 | 61.4 | 0.096 |
| Back | 65 | 78 | 3886 | 2.37 | 4.5 | 0.107 |
| Back | 90 | 109 | 5644 | 24.60 | 2.2 | 0.541 |
| | | | | | STAR | 1.213 |

The resulting Hockey STAR value is 1.213.

Hockey STAR values were 7.098 for hockey helmet A, 12.809 for hockey helmet B, and 1.213 for the football helmet. Lower STAR values equate to lower risk of concussion. Given the assumptions that all players experience an identical head impact exposure to that which was modeled and had the same concussion tolerance to head impact, these STAR values suggest that the concussion rate for players in hockey helmet A would be 44.6% less than that of players in hockey helmet B. Comparing the hockey helmets to the football helmet, players in the football helmet would experience concussions rates 82.9% less than players in hockey helmet A and 90.5% less than players in hockey helmet B.

Advances from Football STAR

Like Football STAR, Hockey STAR system of the present invention is based on two fundamental principles: (1) helmets that lower head acceleration reduce concussion risk and (2) each test is weighted based on how often players experience similar impacts. In one embodiment, the exposure distributions used to weight each impact configuration included both linear and rotational head acceleration from collegiate hockey players. The total number of impacts over one season was also an average of impacts experienced by youth boy's and collegiate men's and women's hockey, since the same helmet models are used for all ages and genders with variations only in helmet size.

In yet another embodiment, the Hockey STAR system of the present invention accounts for a higher underreporting rate of concussion. A bivariate risk function was developed with the assumption that only 10% of concussions sustained by players are diagnosed by physicians. In contrast, the Football STAR risk function assumes that physicians diagnose 50% of concussions sustained by players. Recent studies have suggested that the underreporting rate may be much greater than 50%, and have even suggested that structural changes occur as a result of cumulative head impact exposure in the absence of diagnosed concussion. Because the risk function utilized by Hockey STAR assumes that 90% of concussions go unreported, the Hockey STAR values are not anticipated to be predictive of the number of diagnosed concussions sustained by hockey players, but rather the total number of injuries sustained, diagnosed and undiagnosed.

Biofidelity of Impact Model

In still further embodiments, the biofidelity of the impact model used for Hockey STAR system of the present invention was ensured through appropriate headform selection and comparison of acceleration traces with other data collected from hockey players. A NOC-SAE headform may be used because of its superior helmet fit at the base of the skull, and around the jaw, cheeks, and chin compared to that of the Hybrid III headform. A helmet that does not fit properly can shift on the head during tests, and if the contact area of the helmet padding with the headform varies from what is realistic, the effective stiffness of the padding will vary, potentially resulting in a mischaracterization of a helmet's energy management capabilities.

The headform responses generated from pendulum impacts in the lab were compared to on-ice data by generating corridors from both on-ice player data and ice rink testing with a Hybrid III head (FIGS. 7 and 8). The lab impacts fell within the response corridors generated from both datasets with the exception of the top impacts in the lab compared with the top impacts from ice rink testing. There are two reasons for this difference. The first is that the top impacts for the ice rink testing were pure axial loading to the top of the headform, while the Hockey STAR top location is non-centric and meant to generate rotational acceleration. The second reason is that the ice condition was not tested for the top location on the ice rink, so only boards and glass responses are averaged. These impacts are longer in duration and not representative of the full spectrum of impacts seen by ice hockey players. Overall, this analysis provides further evidence that the laboratory testing is representative of head impacts in hockey.

Star Rating Thresholds

The hockey star methodology of the present invention may ultimately be used to apply star ratings to hockey helmets, which allows consumers to easily compare overall helmet performance between models. While this is already being done with football helmets, the STAR value thresholds used to determine the star ratings of football helmets cannot simply be applied to hockey helmet evaluations due to a number of key differences in the Hockey STAR and Football STAR formulas. The impact exposure weightings are specific to each sport, the test conditions differ, and a more conservative risk function is used in the Hockey STAR methodology. Current football helmet ratings were re-analyzed using a similarly conservative risk function for linear head acceleration. The differences in test conditions were also accounted for by comparing the results of the exemplar football helmet tested under Hockey STAR conditions to the results of the same helmet tested with Football STAR. Proposed star rating thresholds for Hockey STAR are based on these equivalent values (Table 6).

TABLE 6

Comparison of the proposed Hockey STAR rating thresholds to the current thresholds used in Football STAR and Hockey STAR thresholds that are equivalent to current Football STAR thresholds using the proposed methodology.

| Star rating | Current football STAR | Equivalent Hockey STAR | Proposed Hockey STAR |
|---|---|---|---|
| 5 | 0.300 | 1.463 | 1.500 |
| 4 | 0.400 | 2.069 | 2.000 |
| 3 | 0.500 | 2.676 | 2.500 |
| 2 | 0.700 | 3.889 | 4.000 |
| 1 | 1.000 | 5.708 | 6.000 |

To earn a number of stars, a helmet's STAR value must be below the specified threshold.

Exemplar Hockey STAR Results

For the three helmets tested using the Hockey STAR methodology, the Hockey STAR values were 7.098, 12.809, and 1.213 for helmet A, helmet B, and the football helmet, respectively. These values are related to the relative risk of concussion, such that a player wearing helmet A would be 44.6% less likely to sustain a concussion than a player wearing helmet B if both players had the same head impact exposure over one season. Similarly, if a player wore the football helmet and also had the same head impact exposure, that player would be 82.9% less likely to sustain a concussion than a player wearing helmet A, and 90.5% less likely than a player wearing helmet B. Again, it is important to note that these STAR values are not representative of the number of diagnosed concussions players will experience, but rather an overall estimate of undiagnosed and diagnosed injuries combined. While these values are tied to concussion risk, ultimately the rating system identifies helmets that best reduce head acceleration throughout the range of head impacts that hockey player's experience.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above described embodiments, methods, and examples, but by all embodiments and methods within the scope and spirit of the disclosure.

What is claimed is:

1. A method of testing the performance of a helmet comprising the steps of:
    providing a headform for receiving a helmet to be tested, an adaptor for mounting said headform and helmet to a neck on the center of gravity of the headform;
    testing for each helmet the ability to reduce concussion risk by using the following risk function:

$$\sum_{L=1}^{4}\sum_{\theta=1}^{3} E(L, \theta) * R(a, \alpha);$$

wherein L represents head impact locations; θ represents different impact energy levels defined by the angle of impact to the helmet; E represents exposure, or the number of times per season a player is expected to experience an impact similar to a particular condition as a function of location and impact energy; and R is the risk of concussion as a function of linear (a) and angular (α) head acceleration.

2. The method of claim 1 wherein said risk function incorporates both linear (a) and angular (α) head acceleration components and is defined as:

$$R(a,\alpha)=1/1+e^{-(-10.2+0.0433*a+0.000873*\alpha-0.000000920*a\alpha)}.$$

3. The method of claim 1 wherein the impact locations are at the front, side, top, and back of the helmet.

4. The method of claim 3 wherein the front, side and back impacts locations consist of impacts with an elevation less than 65° and are centered on the intersection of the mid-sagittal and coronal planes, but offset by 45° and the top impacts have impacts greater than 65° in elevation.

5. The method of claim 3 wherein the side and top impact locations on the helmet are non-centric such that the direction of force is not aligned with the center of gravity of the headform.

6. The method of claim 3 wherein the front and back impact locations on the helmet are centric such that the direction of force is aligned with the center of gravity of the headform.

7. The method of claim 3 wherein the side and top impact locations on the helmet are non-centric such that the direction of force is not aligned with the center of gravity of the headform and the front and back impact locations on the helmet are centric such that the direction of force is aligned with the center of gravity of the headform.

8. The method of claim 1 including a testing matrix that includes three impact energy levels and four impact locations, for a total of twelve testing conditions per helmet.

9. The method of claim 8 wherein the side, top, front and back of the helmet are the four impacts locations.

10. The method of claim 9 wherein the side and top impact locations are non-centric such that the direction of force is not aligned with the center of gravity of the headform and the front and back impact locations are centric such that the direction of force is aligned with the center of gravity of the headform.

11. The method of claim 1 wherein the impact energy levels are created by a pendulum having an impactor.

12. The method of claim 11 wherein the impacting mass of the impactor is adjustable.

13. The method of claim 11 wherein the impact energy levels created by the pendulum are a low energy level having a 40° pendulum arm angle, a medium energy level having a 65° pendulum arm angle, and a high-energy level having a 90° pendulum arm angle.

14. The method of claim 13 wherein impact energy levels are weighted to determine how frequently a player might sustain a similar impact.

15. The method of claim 13 wherein concussion risks are multiplied by the exposure values for each impact condition to determine incidence values; all incidence values are aggregated to calculate a value for each helmet; and the values for each helmet are averaged to determine a helmet model's overall value.

16. A method of testing the performance of a helmet comprising the steps of:
    testing for each helmet the ability to reduce concussion risk by using the following risk function:

$$\sum_{L=1}^{4}\sum_{\theta=1}^{3} E(L, \theta) * R(a, \alpha);$$

wherein L represents head impact locations; θ represents different impact energy levels defined by the angle of impact to the helmet; E represents exposure, or the number of times per season a player is expected to experience an impact similar to a particular condition as a function of location and impact energy; and R is the risk of concussion as a function of linear (a) and angular (α) head acceleration; and including a testing matrix wherein the testing includes using two helmets of every model tested; each helmets is tested twice and the acceleration values for each helmet's test conditions are averaged for each impact condition prior to using the risk function to determine probability of concussion.

17. The method of claim 16 wherein said risk function incorporates both linear (a) and angular (α) head acceleration components and is defined as:

$$R(a,\alpha) = 1/1 + e^{-(-10.2 + 0.0433*a + 0.000873*\alpha - 0.000000920*a\alpha)}.$$

18. The method of claim 16 wherein the impact energy levels are created by a pendulum having an impactor.

19. The method of claim 18 wherein the impact energy levels created by the pendulum are a low energy level having a 40° pendulum arm angle, a medium energy level having a 65° pendulum arm angle, and a high-energy level having a 90° pendulum arm angle.

20. The method of claim 18 wherein concussion risks are multiplied by the exposure values for each impact condition to determine incidence values; all incidence values are aggregated to calculate a value for each helmet; and the values for each helmet are averaged to determine a helmet model's overall value.

* * * * *